United States Patent [19]

Jacquet et al.

[11] 4,283,384

[45] Aug. 11, 1981

[54] COSMETIC COMPOSITIONS CONTAINING POLYMERS PRODUCED IN THE PRESENCE OF CERIUM IONS

[75] Inventors: Bernard Jacquet, Antony; Jean Mondet, Sevran; Christos Papantoniou, Montmorency, all of France

[73] Assignee: L'Oreal, Paris, France

[21] Appl. No.: 5,919

[22] Filed: Jan. 23, 1979

Related U.S. Application Data

[63] Continuation-in-part of Ser. No. 740,015, Nov. 8, 1976, abandoned.

[51] Int. Cl.³ .................. A61K 7/043; A61K 7/06; A61K 7/08; A61K 7/11
[52] U.S. Cl. .................................. 424/47; 8/405; 8/406; 8/412; 8/421; 424/DIG. 1; 424/DIG. 2; 424/61; 424/70; 424/71; 424/78; 424/168; 424/357; 424/358

[58] Field of Search ............... 424/47, 61, 70, 78, 424/81, 358, DIG. 1, DIG. 2

[56] References Cited

U.S. PATENT DOCUMENTS

| | | | |
|---|---|---|---|
| 2,922,768 | 1/1960 | Mino et al. | 260/29.6 MM |
| 3,954,960 | 5/1976 | Valan | 424/71 |
| 3,990,459 | 11/1976 | Papantoniou | 424/71 |

OTHER PUBLICATIONS

Chemical Abstracts, vol. 71 (1969), p. 124954z.
Chemical Abstracts, vol. 69 (1968), p. 3717z.

*Primary Examiner*—Dale R. Ore
*Attorney, Agent, or Firm*—Cushman, Darby & Cushman

[57] ABSTRACT

A cosmetic composition for application to the hair or skin comprises in an appropriate cosmetic vehicle at least one polymer produced by polymerizing an unsaturated monomer and a compound having at least one OH function, the said polymerization being carried out in an aqueous medium and in the presence of cerium ions.

10 Claims, No Drawings

COSMETIC COMPOSITIONS CONTAINING POLYMERS PRODUCED IN THE PRESENCE OF CERIUM IONS

This is a continuation-in-part of Ser. No. 740,015, filed Nov. 8, 1976 now abandoned which is incorporated by reference herein.

The present invention relates to a cosmetic composition containing a particular type of polymer. These cosmetic compositions comprise, in an appropriate cosmetic vehicle, at least one polymer resulting from the polymerization of an unsaturated monomer and a compound having at least one OH function, the said polymerization being carried out in an aqueous medium in the presence of cerium ions.

Various tests have established that the cosmetic compositions containing these polymers, when applied to the hair, in the form of a hair setting lotion or in the form of a hair lacquer, provide excellent holding power and render the hair soft and shiny.

Moreover, it has been established tht these polymers, when present in other cosmetic formulations such as shampoos, hair rinses or conditioners or hair dye compositions, render the hair easy to untangle and impart thereto excellent brightness characteristics.

Moreover, these polymers can be employed as a primary or secondary component, in milks, creams, lotions or dye foundations, for application to the skin or the face. Their presence in these compositions provides excellent cosmetic characteristics.

These same polymers which can also advantageously replace conventional cosmetic resins presently employed in nail polish compositions impart thereto good adhesion characteristics, long lasting properties and excellent brightness qualities.

In accordance with the present invention, the compound or prepolymer having at least one OH function can be a natural compound, modified or not, or a polymeric or non-polymeric synthetic compound.

Representative natural compounds include, for instance, gelatin, cellulose, starch, modified starch, collagen, chitosans, nitro-cellulose, cellulose ethers and cellulose carrying cationic functions.

Representative synthetic compounds include, for instance:

(i) polymers having a polymeric hydrocarbon chain such as: polyvinyl alcohols; partially hydrolyzed polyvinyl acetates; copolymers of N-vinyl pyrrolidone and vinyl acetate, totally or partially hydrolyzed; copolymers of crotonic acid and vinyl acetate, totally or partially hydrolyzed; polyvinyl pyrrolidone (di-OH); polyacrylamide (di-OH); N-N-dimethyl amino-2-ethyl methacrylate quaternized with ethyl bromide (di-OH); poly butadiene having OH end groups, such as those known under the trade names of "Hycar HTB", sold by Goodrich, "NISSO PBG 2000" sold by Nippon Soda, "R15" sold by Sinclair Koppers, "Butarez HT" sold by Phillips Petroleum, and "Telagen HT" sold by General Tire; polyisobutylene having OH end groups such as those known under the trade name "HTPIB" sold by Enjay Polymer; and copolymers of N-methacryloyl D-glucosamine, such as the copolymers of N-vinyl pyrrolidone/N-methacryloyl D-glucosamine (di-OH or not); and (ii) polymeric compounds having a hydrocarbon chain containing heteroatoms such as, polyethylene glycol, polypropylene glycol, copolymer of polyethylene oxidepolypropylene oxide; copolymer of polyethylene oxidepolysiloxane or polyoxyethylenated nonyl phenols.

Representative non-polymeric compounds include, particularly, pentaerythritol.

Representative unsaturated monomers which are polymerized with the compound having at least one OH function include, for instance:

(a) acrylic or methacrylic acid;

(b) acrylic or methacrylic esters of the formula:

  (I)

wherein R represents hydrogen or methyl and $R_1$ represents linear or branched alkyl having from 1 to 18 carbon atoms. Representative esters include the acrylate or methacrylate of methyl, ethyl, propyl tert-butyl, octyl, dodecyl an octadecyl;

(c) N,N-dialkylamino ethyl acrylic or methacrylic esters of the formula:

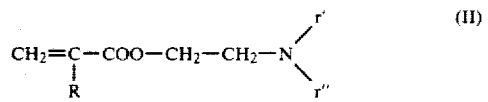  (II)

wherein R hs the same meaning given above and r' and r" each independently represent alkyl having from 1-5 carbon atoms. Included among these compounds are the acrylates or methacrylates of N,N-dimethylamino-2-ethyl acrylates or methacrylates or N,N-diethylamino-2-ethyl acrylates or methacrylates;

(d) hydroxyalkyl acrylic or methacrylic esters of the formula:

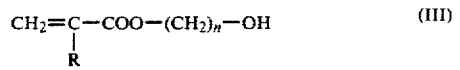  (III)

wherein R has the same meaning given above and n is 2 or 3. Included among these compounds are 2-hydroxy ethyl or 3-hydroxypropyl acrylates or methacrylates;

(e) acrylamide or methacrylamide;

(f) hydroxy alkylacrylamides of the formula:

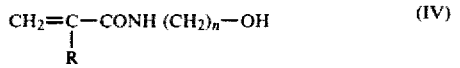  (IV)

wherein R has the same meaning given above and n is 1-3. Included among these compounds are hydroxyethylacrylamide and hydroxypropylacrylamide;

(g) N-alkylacrylamides and methacrylamides of the formula:

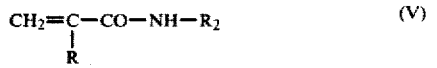  (V)

wherein R has the same meaning given above and $R_2$ represents linear or branched alkyl having from 1-5 carbon atoms. Included among these compounds are N-methylacrylamide and N-tert-butylacrylamide; and (h) N,N-diallyl,N,N-dialkylammonium chlorides or bromides of the formula:

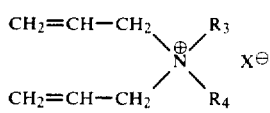

(VI)

wherein R₃ and R₄ each independently represent linear or branched alkyl having from 1-16 carbon atoms and X is Cl or Br. Included among these compounds are N,N-diallyl-N-methyl, N-dodecylammonium chloride or bromide; N,N-diallyl-N-methyl-N-butylammonium chloride or bromide; N,N-diallyl-N-methyl-N-octylammonium chloride or bromide; and N,N-diallyl-N-methyl-N-decylammonium chloride or bromide.

If the compound or prepolymer having at least one OH function is a homopolymer and possesses at one of its ends a single OH function, the polymerization in the presence of an unsaturated monomer such as those listed above produces a sequenced polymer and, more particularly, a bi-sequenced polymer.

On the other hand, if the homopolymer possesses two OH functions, one at each end thereof, a tri-sequenced polymer is obtained.

Thus, when, as the homopolymer having at least two OH functions, polyvinyl pyrrolidone (di-OH) is employed, polymerization of the same with methyl methacrylate (MAM) provides a tri-sequenced polymer which can be schematically represented as follows:

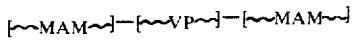

On the other hand, when as the compound having at least one OH function there is employed a copolymer having at least on one of its ends an OH function and also at least one lateral OH function, the polymerization in the presence of an unsaturated monomer provides a polymer which is both sequenced and graft.

Thus, the use of a compound having OH functions of the type indicated above, i.e. a copolymer of N-vinyl pyrrolidone/N-methacryloyl D-glucosamine (di-OH) of the following formula:

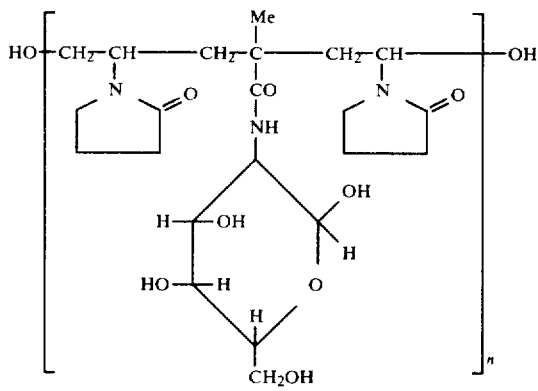

provides on copolymerization with, for example, methyl methacrylate, a compound having on the one hand polymethylmethacrylate (PMAM) sequences at each end of the polymer chain and additionally PMAM grafts on one or more of the OH functions of the glucosamine molecule.

In another embodiment of the present invention, the compound having at least one OH function can be a copolymer free of terminal OH groups, but having, on the contrary, at least one lateral OH function so that the presence of an unsaturated monomer, the polymerization provides a graft polymer only.

Thus, the use of a copolymer having at least one lateral OH function, i.e. a polymer having the following formula formula:

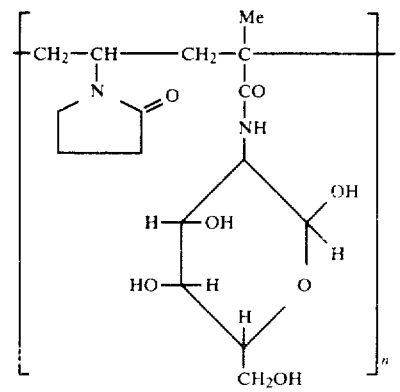

provides on copolymerization with methylmethacrylate a copolymer having PMAM grafts on one or more of the glucosamine OH functions.

Further, in another embodiment of the present invention, the compound having at least one OH function can be a non-polymeric compound, such as, for example, pentaerythritol, a compound which has four OH functions. The polymerization of this compound with an unsaturated monomer, such as methyl methacrylate, provides a compound having PMAM grafts on one or more of the OH functions. Polymers of this type are called "starred polymers".

As will be seen from the Examples below, the proportions of reactants used to form the polymers in accordance with invention can vary widely, that is, the compound having at least one OH function may constitute from about 15 to 95% by weight of reactants and the unsaturated monomer may comprise from 5 to about 85% by weight of the reactants.

The molecular weight of the polymer utilized in the cosmetic composition of this invention can vary significantly, and the choice of any particular molecular weight can be dictated by the particular type of cosmetic formulation in which it is incorporated. Further, the molecular weight of the polymer can be dependent on the choice of the particular reactants employed to produce the same such as the polymeric or non-polymeric content of the prepolymer or compound and on the number of sequences or of the degree or amount of grafting desired.

The polymers employed in accordance with the present invention, be they sequenced, sequenced and grafted, grafted, or starred, are prepared simply by reacting in an aqueous solution the compound or prepolymer having at least one oh function with an unsaturated monomer in the presence of an effective amount of cerium salt such as, for example, cerium ammonium nitrate [(NH₄)₂Ce(NO₃)₆].

The operating conditions for this process which are known, see L. J. Guilbault et al, J. Macro. Sci. Chem. A7(8), P. 1.581 (1973) are as follows:

The prepolymer or compound and the unsaturated monomer or monomers to be polymerized are placed in an aqueous solution (distilled water) in a reactor fitted with a stirrer and a nitrogen lead-in tube. To this mixture, there is introduced an amount of cerium ammonium nitrate sufficient to form the desired number of sequences and/or the amount or degree of grafting. Obviously, then the quantity of catalyst can be significantly varied, depending on the ultimate polymer desired for inclusion in a particular type cosmetic formulation. In a preferred manner, the cerium ammonium nitrate is introduced in solution in normal nitric acid.

The resulting reaction mixture is then stirred for a time varying from 2 to 48 hours, either at ambient temperature or at a temperature between 40° and 80° C.

After the termination of the polymerization reaction, the resulting polymer is then precipitated with an organic material such as, for example, ether, isopropyl alcohol, acetonitrile, acetone or a mixture thereof.

Importantly, the preparation of certain prepolymers must be carried out under special conditions, that is, in an aqueous solution in the presence of $H_2O_2$ which serves as an initiator, and with a compound such as borax so as to provide on the polymeric chain some terminal OH groups. Such is the case, for example, in the preparation of polyvinyl pyrrolidone (di-OH) or polyacrylamide (di-OH) or the copolymer of N-vinylpyrrolidone/N-methacryloyl D-glucosamine (di-OH).

The exact structure of the desired polymers of the present invention has not yet been determined with exactitude since the radical formed by the reduction of $Ce^{IV}$ to $Ce^{III}$ in the presence of at least one OH function can be situated either on the oxygen of the OH or on the adjacent carbon.

The cosmetic compositions of the present invention can contain the polymers defined above either as the principal active component, or as an additive.

These cosmetic compositions can be provided in the form of aqueous, alcoholic or hydroalcoholic solutions, the alcohol being principally a lower alkanol such as ethanol or isopropanol, or in the form of creams, gels, emulsions, milks or in the form of an aerosol also containing a propellant, or even in the form of a nail polish.

The adjuvants generally included in the cosmetic compositions of the present invention are, for example, perfumes, dyes, preservatives, sequesterants, thickening agents and the like.

The cosmetic compositions of the present invention can be the ready-to-use type compositions or they can be concentrates which require dilution before use. Thus, the cosmetic compositions of the present invention need not be limited to any particular polymer concentration.

Generally, however, in the cosmetic compositions of the present invention, the polymer is present in an amount between 0.1 and 15 weight percent thereof and preferably between 0.5 and 10 weight percent.

These cosmetic compositions exhibit significantly interesting cosmetic properties when they are applied to the hair. Thus when they are applied to the hair, they substantially improve the qualities of the hair and facilitate untangling wet or moist hair.

Thus, in one embodiments of the present invention, the cosmetic compositions are principally cosmetic compositions for the living human hair containing at least one polymer as described above. Further, these cosmetic compositions for the hair generally include at least one adjuvant conventionally employed in such type compositions.

These cosmetic compositions for the hair can be provided in the form of an aqueous, alcoholic or hydroalcoholic solution (the alcohol being a lower alkanol such as ethanol or isopropanol), or in the form of a cream, a gel or an emulsion or even in the form of a spray. They can also be packaged under pressure in an aerosol container so as to form an aerosol which also contains a propellant, such as for example, nitrogen, nitrogen pentoxide or chlorofluoronated hydrocarbons of the Freon type, such as Freon 11 and Freon 12, or a mixture of these propellants.

The adjuvants generally provided in the cosmetic compositions for the hair in accordance with the present invention can be, for example, perfumes, dyes, preservatives, sequesterants, thickening agents and emulsifying agents.

The polymers can be provided, in the cosmetic compositions for the hair of this invention, either as an additive, or as the principal active component in hair setting lotions, in hair treating lotions, in hair styling creams or gels, or as an additive in shampoos, hair setting lotions, permanent waving formulations, hair restructuring agents, hair treating lotions or hair lacquer compositions.

The cosmetic compositions for the hair of the present invention are then principally:

(a) hair treating or lotion compositions comprising, as the active component, at least one polymer according to the invention in an aqueous or hydroalcoholic solution. The amount of polymer can vary between 0.1 to 10% by weight and preferably between 0.1 and 5% by weight.

The pH of these lotions is close to neutral and can vary for example from 6 to 8. If necessary, the pH can be adjusted to the desired value, by adding either an acid such as citric acid or a base, principally an alkanolamine such as monoethanolamine or triethanolamine.

To treat the hair with such a lotion, the same is applied to damp hair and is permitted to remain in contact therewith for 3 to 15 minutes. Thereafter the hair is thoroughly rinsed, and if desired, set in a conventional manner;

(b) a shampoo composition comprising at least one polymer according to the invention and a cationic, non-ionic or anionic detergent.

Representative cationic detergents include, principally, long chain quaternary ammoniums, esters of fatty acids and amino alcohols or amine polyethers.

Representative non-ionic detergents include, principally, esters of polyols and sugars, the condensation products of ethylene oxide on fatty bodies, on long chain alkyl phenols, on long chain mercaptans or on long chain amides and the polyhydroxylated polyethers or fatty alcohols.

Representative anionic detergents include, principally, alkaline salts, ammonium salts or salts of amines or of amino alcohols with fatty acids such as oleic acid, ricinoleic acid, copra oil acid, hydrogenated copra oil acid, alkaline salts, ammonium salts or salts of amino alcohols and the sulfates of fatty alcohols, principally $C_{12}$-$C_{14}$ and $C_{16}$ fatty alcohols; alkaline salts, magnesium salts, ammonium salts or amino alcohol salts of the sulfates of oxyethylenated fatty alcohols; the condensation products of fatty acids with isethionates, taurine, methyl taurine, or sarcosine etc; the alkylbenzenesulfonates, notably those wherein the alkyl moiety has 12 carbon atoms; the alkylarylpolyether sulfates and monoglyceride sulfates. All these anionic detergents, as well as numerous others not cited here, are well kwown and are described in the literature.

The shampoo composition of the present invention can also contain various adjuvants, for example, perfumes, dyes, preservatives, thickening agents, foam stabilizers, softening agents or other cosmetic resins. In these shampoo compositions, the concentration of the detergent is generally between 5 and 50 percent by weight and the polymer concentration is between 0.1 and 10 weight percent and preferably between 0.1 and 5 weight percent of said composition;

(c) a hair setting lotion, notably for sensitized hair, comprising at least one polymer of this invention, in aqueous, alcoholic or hydroalcoholic solution. These compositions can also contain other cosmetic resins. The polymer concentration in these hair setting lotions can vary generally between 0.1 and 5 weight percent and, preferably, between 0.2 to 3 weight percent thereof. The pH of these hair setting lotions can range generally between 3 and 9 and preferably between 4.5 and 7.5. The pH, if desired, can be adjusted for example by adding an alkanolamine such as monoethanolamine or triethanolamine;

(d) hair dye compositions comprising at least one polymer according to the invention, a dye agent and an appropriate vehicle. Preferably, the vehicle chosen is one which provides the composition in cream form. The concentration of the polymer in these hair dye compositions can vary between 0.5 and 15 weight percent, and preferably between 0.5 and 10 weight percent thereof.

When an oxidation dye is employed, the dye composition can be packaged in two parts, one part containing $H_2O_2$ and the other part the remaining components. The two parts are admixed at the time of use; and (e) hair lacquer compositions comprising an alcoholic or hydroalcoholic solution of at least one polymer of the present invention, this solution being packaged in an aerosol container under pressure together with a conventional aerosol propellant.

The aerosol lacquer according to the present invention can be prepared by adding the polymer of the invention to a mixture of an anhydrous aliphatic alcohol such as ethanol or isopropanol and a propellant or a mixture of liquified propellants such as halogenated hydrocarbons, of the trichlorofluoromethane or dichlorodifluoromethane type or their mixtures.

In these hair lacquer compositions, the polymer concentration generally ranges between 0.1 and 3 weight percent thereof. It is also permissible to add to these hair lacquer compositions such adjuvants as dyes, plasticizers or any other conventional adjuvant.

The polymers of the present invention also exhibit interesting cosmetic characteristics when they are applied to the skin. Principally they favor the hydration of the skin, and thus avoid its drying out. Further, they impart to the skin a significant softness to the touch characteristic.

Thus, the cosmetic compositions of the present invention can be cosmetic compositions for the skin which include at least one polymer according to the invention. Further, these compositions can contain at least one adjuvant conventionally employed in cosmetic compositions for the skin and can be provided, for example, in the form of creams, gels, emulsions or as an aqueous, alcoholic or hydroalcoholic solution.

The polymer concentration in these compositions for the skin can vary generally between 0.1 and 10 weight percent thereof.

The adjuvants generally present in these cosmetic compositions are for example perfumes, dyes, preservatives, thickening agents, sequesterants, emulsifying agents and the like.

These compositions for the skin constitute, principally, creams or treating lotions for the hands or face, anti-solar creams, dye foundation creams and make-up remover milks and can be prepared in accordance with conventional procedures.

For example, to obtain a cream, an aqueous phase containing in solution the polymer of the present invention and optionally other components or adjuvants is emulsified with an oily phase.

Representative oily phases can include, for instance, paraffin oil, petrolatum oil, sweet almond oil, avocado oil, olive oil, esters of fatty acids such as glyceryl monostearate, ethyl or isopropyl palmitate and alkyl myristates such as propyl, butyl or cetyl myristate. Further fatty alcohols such as cetyl alcohol or waxes such as beeswax can also be included.

The compositions according to the present invention can also be provided in the form of nail polish and contain preferably from 3 to 15 percent by weight of the polymer of the present invention in combination with a plasticizing agent, a film forming agent and a solvent system, i.e. conventional solvents and/or diluents for this type of composition. The solvent system comprises from 60 to 80 weight percent of the nail polish composition. In certain cases these nail polish compositions can also contain a dye in an amount ranging from 0.05 to 6 percent by weight relative to the total weight of the nail polish composition.

The nail polish composition of the present invention provides excellent brightness and durability.

The following non-limiting examples illustrate the preparation of the polymers and the cosmetic compositions of the present invention.

EXAMPLES OF PREPOLYMER PREPARATION

EXAMPLE 1

Preparation of polyvinylpyrrolidone prepolymer containing an OH function at each end of the chain thereof Into a 1 liter round bottom flask, 100 g of freshly distilled N-vinyl-pyrrolidone, 500 g of distilled water and 1.5 g of borax $(Na_2B_4O_7.10H_2O)_n$ are introduced. The resulting reaction mixture is heated with stirring to 40° C. under a current of nitrogen.

After dissolution of the borax, 1 ml of $H_2O_2$ (110 volumes) is added to the reaction mixture and the temperature thereof is maintained at 40° C. for 7 hours. The resulting polymer is precipitated in acetone and dried under reduced pressure, yielding 99 g of pure polymer having a viscosity of 4.5 cpo at 34.6° C. in a 5% solution in water.

EXAMPLE 2

Preparation of N-vinylpyrrolidone/N-methacryloyl D-glucosamine prepolymer

Into a 500 ml round bottom flask fitted with a stirrer and a nitrogen lead-in tube, 100 g of ethanol, 95 g of distilled N-vinylpyrrolidone, 5 g of N-methacryloyl D-glucosamine and 1 g of azo-bisisobutyronitrile are introduced.

The resulting mixture is heated to 80° C. for 16 hours and the resulting polymer which is precipitated in acetone for a 60% yield, has a viscosity of 1.8 cpo at 34.6° C. in a 5% solution in water.

EXAMPLE 3

Preparation of partially hydrolyzed N-vinylpyrrolidone/vinyl acetate prepolymer

Into a 2 liter round bottom flask 800 ml of ethanol, 12.8 g of sodium hydroxide pellets and 80 g of a copolymer composed of 70% N-vinylpyrrolidone and 30% vinyl acetate are introduced. The resulting reaction mixture is maintained with stirring at 30° C. for 2 hours and is then poured into 8 liters of diethyl ether to precipitate the desired polymer. After filtration the polymer is dried under reduced pressure. Yield: 95%.

EXAMPLE 4

Preparation of a partially hydrolyzed crotonic acid/vinyl acetate prepolymer

The procedures of Example 3 are repeated except that there is employed a 90% vinyl acetate-10% crotonic acid copolymer. Yield: 95%.

EXAMPLES 5-12

Table I below illustrates the preparation of other prepolymers prepared in accordance with the method of Examples 1 or 2 above.

Preparation of the Catalyst

The solution of cerium ammonium nitrate (CAN) is prepared by dissolving 58.5 g of cerium ammonium nitrate in a 1 N nitric acid solution and adding a sufficient amount of said nitric acid solution to make 1 liter.

EXAMPLE 13

Preparation of a trisequenced copolymer of polymethyl methacrylate/poly N-vinylpyrrolidone/polymethyl methacrylate (PMAM-PVP-PMAM)

Into a 2 liter round bottom flask fitted with a stirrer and a nitrogen lead-in tube, 1250 ml of distilled water and 95 g of polyvinylpyrrolidone (di-OH) prepared in accordance with Example 1 are introduced. There are then introduced 5 g of distilled methyl methacrylate and 50 ml of a solution of cerium ammonium nitrate in nitric acid. The reaction mixture is maintained with stirring for 4 hours at ambient temperature after which it is poured into an ethyl ether-isopropanol mixture. The resulting polymer which precipitates is recovered, dissolved in dimethyl formamide and reprecipitated in sulfuric ether. Yield: 70%.

EXAMPLE 14

Preparation of a sequenced and graft 50:50 copolymer of polyvinyl alcohol—N,N-dimethyl-2-aminoethyl polymethacrylate quaternized with dimethyl sulfate Into a 2 liter round bottom flask fitted with a stirrer and a nitrogen lead-in tube, 670 ml of water and 50 g of

TABLE I

| Example No. | Monomer | Amount (g) | AIBN [a] | $H_2O_2$ 110 vol (ml) | Borax (g) [b] [c] | Water (ml) | Ethanol | Temperature of Reaction (C.°) | Duration of Reaction (hours) | Precipitant | Yield (%) | Viscosity (cPo) [d] |
|---|---|---|---|---|---|---|---|---|---|---|---|---|
| 5 | N-vinyl pyrrolidone (di-OH) | 100 | | 5 | 2.5 | 100 | | 40 | 7 | acetone | 99 | 1.9 |
| 6 | N-vinyl pyrrolidone (di-OH) | 100 | | 20 | 2 | 80 | | 40 | 6 | acetone | 98 | 2.07 |
| 7 | N-vinyl pyrrolidone (di-OH) | 1000 | | 50 | 10 | 1000 | | 40 | 7 | acetone | 90 | 1.42 |
| 8 | N-vinyl pyrrolidone (di-OH) | 100 | | 2 | 1 | 100 | | 40 | 6 | acetone | 95 | 2.28 |
| 9 | N-vinyl pyrrolidone (di-OH) | 100 | | 10 | 4 | 500 | | 40 | 24 | acetone | 80 | 3.95 |
| 10 | N,N-dimethyl 2-amino-ethyl methacrylate (di-OH), quaternized with ethyl bromide | 100 | | 10 | 4 | 500 | | 40 | 24 | ethanol | 70 | 2.0 |
| 11 | N-vinyl pyrrolidone/ N-methacryloyl D-glucosamine | 90 / 10 | 1 | | | | 100 | 80 | 16 | acetone | 70 | 1.85 |
| 12 | N-vinyl pyrrolidone/ N-methacryloyl D-glucosamine (di-OH) | 80 / 20 | 1 | | | 500 | | 40 | 16 | acetone | 60 | |

[a] Azobisisobutyronitrile
[b] $Na_2B_4O_7 \cdot 10H_2O$
[c] The pH is maintained greater than 9 during the polymerization by the supplemental additions of borax.
[d] In a 5% solution in water at 34.6° C.

Preparation of Polymers—all the initial reactants employed are purified.

polyvinyl alcohol sold by Prolabo under the trade name Rhodovial A/125P are introduced. The resulting mixture is heated with stirring to 80° C. until the polyvinyl alcohol is completely dissolved. The reaction mixture is then cooled to 20° C. and there are introduced therein 50 g of N,N-dimethyl 2-amino ethyl methacrylate quaternized with dimethyl sulfate and 50 ml of a solution of cerium ammonium nitrate in nitric acid.

The reaction mixture is maintained with stirring for 16 hours at ambient temperature after which the polymer is precipitated in a 3:2 mixture of acetone and isopropanol. The resulting polymer is then filtered and dried under reduced pressure. Yield: 98%.

EXAMPLE 15

Preparation of a sequenced and graft, 50/50 copolymer of polyvinyl alcohol and N-vinyl pyrrolidone The procedures of Example 14 are repeated except that 50 g of distilled N-vinylpyrrolidone are polymerized with 50 g of polyvinyl alcohol over a 16 hour period. The resulting polymer is precipitated in a 3/2 acetone/isopropanol mixture.

EXAMPLE 16

Preparation of a trisequenced copolymer by cyclopolymerization of N,N-diallyl-N,N-dimethyl ammonium bromide with poly-N-vinylpyrrolidone (di-OH)

Into a 500 ml round bottom flask fitted with a stirrer and a nitrogen lead-in tube, 500 ml of distilled water and 25 g of polyvinylpyrrolidone (di-OH) prepared according to Example 1 are introduced. To the resulting mixture there are added 25 g of N,N-diallyl, N,N-dimethyl ammonium bromide and 25 ml of a solution of cerium ammonium nitrate in nitric acid. The resulting mixture which is maintained with stirring at 40° C. for 48 hours is then poured into acetonitrile. The precipitated polymer is recovered and dried under reduced pressure, providing 15 g of pure polymer. Yield: 30%.

EXAMPLE 17

Preparation of a trisequenced copolymer by cyclopolymerization of N,N-diallyl-N-dodecyl-N-methyl ammonium bromide with poly N-vinylpyrrolidone (di-OH)

The procedures of Example 16 are repeated except that 25 g of N,N-diallyl N-dodecyl N-methyl ammonium bromide are polymerized with 25 g of poly N-vinylpyrrolidone (di-OH). The resulting polymer is precipitated in acetonitrile and recovered therefrom, providing 10 g of pure polymer. Yield: 20%.

EXAMPLES 18 to 52 (see Table II below)

TABLE II

| Example No. | Form of the Polymer Obtained | Nature of the Prepolymers and the Monomers | Amount (g) | $H_2O$ (ml) | NAC (ml) | Temperature of Reaction (C.°) | Duration of Reaction (hours) | Yield of the Polymerization | Precipitant |
|---|---|---|---|---|---|---|---|---|---|
| 18 | sequence | Prepolymer of Example 8 | 9 | 125 | 5 | 30 | 3½ | | acetonitrile |
| | | Methyl methacrylate | 1 | | | | | | |
| 19 | sequence | Prepolymer of Example 6 | 5 | 125 | 5 | 30 | 24 | | ethyl ether |
| | | N,N-dimethylamino-2-ethyl methacrylate quaternized with ethyl bromide | 5 | | | | | | |
| 20 | sequence | Prepolymer of Example 6 | 9 | 125 | 5 | 30 | 24 | | ethyl ether |
| | | N,N-dimethylamino-2-ethyl methacrylate quaternized with ethyl bromide | 1 | | | | | | |
| 21 | sequence | Prepolymer of Example 8 | 9 | 125 | 5 | 30 | 16 | | 1/1 mixture of ethyl ether/isopropanol |
| | | Acrylic acid | 1 | | | | | | |
| 22 | sequence | Prepolymer of Example 6 | 5 | 125 | 5 | 30 | 16 | | ethyl ether |
| | | Acrylamide | 5 | | | | | | |
| 23 | sequence | Prepolymer of Example 8 | 8 | 125 | 5 | 30 | 24 | | 1/1 mixture of ethyl ether/isopropanol |
| | | Acrylamide | 2 | | | | | | |
| 24 | sequence | Prepolymer of Example 8 | 150 | 2700 | 150 | 40 | 48 | 45 | acetonitrile |
| | | N,N-diallyl N,N-dimethyl ammonium bromide | 150 | | | | | | |
| 25 | sequence | Prepolymer of Example 7 | 50 | 900 | 50 | 40 | 18 | 75 | acetone |
| | | Lauryl methacrylate | 50 | | | | | | |
| 26 | sequence | Prepolymer of Example 9 | 50 | 1100 | 50 | 40 | 24 | 90 | acetone |
| | | N,N-dimethylamino-2-ethyl methacrylate quaternized with ethyl bromide | 50 | | | | | | |
| 27 | sequence | Prepolymer of Example 10 | 9 | 125 | 5 | 30 | 4 | | acetone |
| | | Methyl methacrylate | 1 | | | | | | |
| 28 | sequence | Prepolymer of Example 2 | 8 | 125 | 5 | 30 | 24 | 80 | acetone |
| | | Methyl methacrylate | 2 | | | | | | |
| | | Prepolymer | 9 | | | | | | |

TABLE II-continued

| Example No. | Form of the Polymer Obtained | Nature of the Prepolymers and the Monomers | Amount (g) | H₂O (ml) | NAC (ml) | Temperature of Reaction (C.°) | Duration of Reaction (hours) | Yield of the Polymerization | Precipitant |
|---|---|---|---|---|---|---|---|---|---|
| 29 | sequence | of Example 11 Acrylamide | 1 | 125 | 5 | 30 | 24 | 85 | acetone |
| 30 | sequence and graft | Prepolymer of Example 12 Methyl methacrylate | 8 2 | 125 | 5 | 30 | 60 | 80 | acetone |
| 31 | sequence and graft | Polyvinyl alcohol (Rhodoviol 4/125 P) N,N-dimethylamino-2-ethyl methacrylate quaternized with ethyl bromide | 20 80 | 670 | 50 | 25 | 16 | 98 | 3/2 mixture of acetone/ isopropanol |
| 32 | sequence and graft | Polyvinyl alcohol (Rhodoviol 4/125 P) N,N-dimethylamino-2-ethyl methacrylate quaternized with dimethyl sulfate | 20 80 | 670 | 50 | 25 | 16 | 70 | 3/2 mixture of acetone/ isopropanol |
| 33 | sequence and graft | Polyvinyl alcohol (Rhodoviol 4/125 P) Acrylamide | 15 15 | 200 | 12 | 25 | 4 | 60 | acetone |
| 34 | sequence | Polyethylene glycol (MW = 20,000) N,N-dimethylamino-2-ethyl methacrylate quaternized with ethyl bromide | 50 50 | 900 | 50 | 30 | 48 | 20 | acetone |
| 35 | starred | Pentacrythritol N,N-dimethylamino-2-ethyl methacrylate quaternized with ethyl bromide | 14 80 | 900 | 10 | 30 | 48 | 45 | acetone |
| 36 | sequence and graft | Methyl cellulose (Methocel A-15) N,N-dimethylamino-2-ethyl methacrylate quaternized with ethyl bromide | 35 115 | 900 | 30 | 30 | 24 | 40 | heptane/ isopropanol |
| 37 | sequence and graft | Methylhydroxy-propylcellulose (Pharmacoat 603) N,N-dimethylamino-2-ethyl methacrylate quaternized with ethyl bromide | 35 115 | 900 | 30 | 30 | 24 | 40 | heptane/ isopropanol |
| 38 | sequence and graft | Hydroxyethyl-cellulose (Cellosize WP-09) N,N-dimethylamino-2-ethyl methacrylate quaternized with ethyl bromide | 35 115 | 900 | 30 | 30 | 24 | 40 | heptane/ isopropanol |
| 39 | sequence and graft | Methylhydroxy-butylcellulose (Methocel HB) N,N-dimethylamino-2-ethyl methacrylate quaternized with ethyl bromide | 35 115 | 900 | 30 | 30 | 24 | 40 | heptane/ isopropanol |
| 40 | sequence and graft | Methylhydroxy-propylcellulose (Pharmacoat 603) Acrylamide | 80 70 | 750 | 37.5 | 30 | 24 | 40 | ethyl ether/ isopropanol |
| 41 | sequence and graft | Methylcellulose (Methocel A-15) Acrylamide | 80 70 | 1150 | 37.5 | 30 | 24 | 65 | ethyl ether/ isopropanol |
| 42 | sequence and graft | Methylhydroxy-butylcellulose (Methocel HB) Acrylamide | 13 12 | 350 | 6.25 | 30 | 24 | 20 | ethyl ether/ isopropanol |
| 43 | sequence and graft | Carboxymethyl cellulose (Finn Fix 300) Acrylamide | 80 70 | 750 | 37.5 | 30 | 24 | 95 | ethyl ether/ isopropanol |
| 44 | sequence and graft | Hydroxyethyl-cellulose (Cellosize WP-09) Acrylamide | 80 70 | 1150 | 37.5 | 30 | 24 | 90 | ethyl ether/ isopropanol |
| 45 | sequence | Collagen (C-1633 type IV) | 1 | 10 | 0.5 | 30 | 24 | 40 | acetone |

TABLE II-continued

| Example No. | Form of the Polymer Obtained | Nature of the Prepolymers and the Monomers | Amount (g) | H₂O (ml) | NAC (ml) | Temperature of Reaction (C.°) | Duration of Reaction (hours) | Yield of the Polymerization | Precipitant |
|---|---|---|---|---|---|---|---|---|---|
| | and graft | N,N-dimethylamino-2-ethyl methacrylate quaternized with ethyl bromide | 1 | | | | | | |
| 46 | sequence and graft | Gelatin (ASF) | 5 | 125 +25 ml EtOH | 5 | 40 | 24 | 50 | ethyl ether/ isopropanol |
| | | N,N-dimethylamino-2-ethyl methacrylate quaternized with ethyl bromide | 5 | | | | | | |
| 47 | sequence and graft | Prepolymer of Example 3 | 29 | 450 | 30 | 30 | 24 | 30 | acetone/ isopropanol |
| | | N,N-dimethylamino-2-ethyl methacrylate quaternized with ethyl bromide | 30 | | | | | | |
| 48 | sequence and graft | Prepolymer of Example 4 | 30 | 450 | 30 | 30 | 48 | 35 | ethyl ether/ isopropanol |
| | | N,N-dimethylamino-2-ethyl methacrylate quaternized with ethyl bromide | 30 | | | | | | |
| 49 | sequence and graft | Gelatin (ASF) | 30 | 450 | 30 | 30 | 48 | 35 | acetone |
| | | Methyl methacrylate | 30 | | | | | | |
| 50 | sequence and graft | Methylhydroxy-butylcellulose (Methocel HB) | 70 | 850 | 25 | 30 | 24 | 30 | acetone |
| | | Hexyl methacrylate | 30 | | | | | | |
| 51 | sequence and graft | Methylhydroxy-butylcellulose (Methocel HB) | 9 | 350 | 6.25 | 30 | 48 | 25 | ethyl ether/ isopropanol |
| | | N-tertiobutyl acrylamide | 1 | | | | | | |
| 52 | sequence | Prepolymer of Example 4 | 9 | 125 | 5 | 30 | 48 | 20 | ethyl ether |
| | | N-tertiobutyl acrylamide | 1 | | | | | | |

In the polymerizations of the foregoing Examples, the amount of the compound having at least one OH function which was polymerized with the unsaturated monomer ranged from about 15 to 95 percent by weight based on the combined weight of the compound having at least one OH function and the unsaturated monomer. The amount of unsaturated monomer in the foregoing polymerization was from 5 to about 85% by weight, based on the combined weight of unsaturated monomer and the compound having at least one OH function.

EXAMPLES OF PREPARING COSMETIC COMPOSITIONS

EXAMPLE A

A hair setting lotion is prepared by admixing the following components:
Polymer of Example 13: 2 g
Perfume: 0.1 g
Ethyl Alcohol: 50 g
Water, q.s.p.: 100 g This hair setting lotion when applied in a conventional manner to the hair imparts thereto a shiny appearance. The resulting hair set exhibits excellent holding characteristics.

This example is repeated except that the polymer of Example 13 is replaced by the same amount of any one of the polymers of Examples 14–16 and 25–30.

EXAMPLE B

A hair setting lotion is prepared by admixing the following components:
Polymer of Example 32: 3.5 g
Perfume: 0.1 g
Dye, sufficient to color the lotion: 0.2 g
Isopropyl alcohol: 50 g
Water, q.s.p.: 100 g After impregnating the hair with lotion of this example, the hair is rolled up on hair setting rollers, having a diameter of 15–30 mm, and then dried by an external source of heat. After removing the rollers, an excellent setting with very good holding properties is obtained.

This example is repeated except that the polymer of Example 32 is replaced with the same amount of any one of the polymers of Examples 15 and 33–43. Equally favorable results are achieved in each instance.

EXAMPLE C

A hair setting lotion is prepared by admixing the following components:
Polymer of Example 28: 3 g
Ethyl alcohol: 50 g
Perfume: 0.2 g
Water, q.s.p.: 100 g This example is repeated except that the 3 g of the polymer of Example 28 is replaced by the same amount of one of the copolymers of Example 16, 17 and 43–52.

EXAMPLE D

An aerosol hair lacquer composition is prepared by admixing the following components:
Polymer of Example 13: 8 g
Perfume: 0.2 g
Absolute ethyl alcohol, q.s.p.: 100 g 25 g of this solution are then packaged in an aerosol container under pressure together with 47 g of trichlorofluoromethane and 28 g of dichlorodifluoromethane.

After spraying the resulting lacquer on the hair, the hair is shiny, soft to the touch and the resin is easily removed by brushing.

This example is repeated except that the polymer of Example 13 is replaced by the same amount of one of the polymers of Examples 18, 22 and 23. Equally favorable results are achieved.

EXAMPLE E

An aerosol hair lacquer composition is prepared by admixing the following components:
Polymer of Example 28: 7.2 g
Perfume: 0.3 g
Isopropyl alcohol, q.s.p.: 100 g 25 g of this solution are packaged in an aerosol container under pressure together with 47 g of trichlorofluoromethane and 28 g of dichlorodifluoromethane.

After spraying the above composition on the hair, the hair is shiny and soft to the touch.

This example is repeated except that the polymer of Example 28 is replaced by the same amount of one of the polymers of Examples 22, 23 and 24. Equally favorable results are achieved.

EXAMPLE F

A film forming body milk is prepared by admixing the following components:
Di-ethyl hexyl adipate: 4.8 g
Stearic acid: 2.9 g
Lanolin alcohol oxyethylenated with 5 moles of ethylene oxide: 0.5 g
Cetyl alcohol: 0.4 g
Glycerol stearate: 1.0 g
Triethanolamine: 0.95 g
Propylene glycol: 4.8 g
Polymer of Example 14: 0.5 g
Preservative, an effective amount
Perfume, an effective amount
Sterile, demineralized water, q.s.p.: 100 g This example is repeated except that the polymer of Example 14 is replaced by the same amount of any one of the polymers of Examples 15–20 and 33–43.

EXAMPLE G

A film-forming skin cream is prepared by admixing the following components:
Paraffin oil: 30.0 g
Stearic acid: 8.0 g
Triethanolamine: 1.0 g
Polymer of Example 32: 0.5 g
Preservative, an effective amount
Perfume, an effective amount
Sterile demineralized water, q.s.p. 100 g This example is repeated except that the polymer of Example 32 is replaced by the same amount of any one of the polymers of Examples 44–52 or Examples 13–20.

EXAMPLE H

A lotion for the skin is prepared by admixing the following components:
Polymer of Example 32: 1.0 g
Propylene glycol: 2.0 g
Ethanol: 10.0 g
Methyl parahydroxybenzoate: 0.2 g
Perfume, an effective amount
Dye, an effective amount to color the lotion
Sterile, demineralized water, q.s.p. 100 g Initially the polymer of Example 32 is dissolved in an aqueous solution of the preservative (all of the water and the preservative) at 60° C. Thereafter the solution is cooled and the remaining components are added thereto with moderate stirring.

This example is repeated except that the polymer of Example 32 is replaced by the same amount of any one of the polymers of Examples 13, 18–24, 26–31 and 33–48.

EXAMPLE I

A beauty mask composition is prepared by admixing the following components:
Polymer of Example 14: 20.0 g
Propylene glycol: 5.0 g
Methyl parahydroxybenzoate: 0.2 g
Ethanol: 15.0 g
Kaolin: 10.0 g
Titanium oxide: 0.5 g
Triethanolamine lauryl sulfate: 6.0 g
Perfume, an effective amount
Sterile, demineralized water: 100 g Initially the polymer of Example 14 is dissolved in an aqueous solution of the preservative (all of the water and the preservative) at 60° C. Thereafter the solution is cooled and the remaining components are added thereto with moderate stirring.

This example is repeated except that the polymer of Example 14 is replaced by the same amount of any one of the polymers of Examples 15–20 and 44–52.

EXAMPLE J

A dye foundation composition is prepared by admixing the following components:

| | |
|---|---|
| Partial glyceride of fatty acid | 9.00 g |
| Cetyl stearyl alcohol ethoxylated with 10 moles of ethylene oxide | 4.00 g |
| Paraffin oil | 18.00 g |
| Polymer of Example 14 | 1.00 g |
| Magnesium and aluminum silicates | 0.75 g |
| Rhodorsil (anti-foaming agent) | 0.20 g |
| Alkyl parahydroxybenzoate | 0.20 g |
| Water, permuted | 66.85 g |
| Dyes, mineral | 5.00 g |
| | 105.00 g |

This example is repeated except that the polymer of Example 14 is replaced by the same amount of any one of the polymers of Examples 27–37 and 43–52.

EXAMPLE K

A dye foundation composition is prepared by admixing the following components:

| | |
|---|---|
| Partial glyceride of fatty acid | 9.00 g |
| Cetylstearyl alcohol ethoxylated with 10 moles of ethylene oxide | 4.00 g |
| Paraffin oil | 18.00 g |
| Polymer of Example 32 | 1.00 g |
| Magnesium and aluminum silicates | 0.75 g |

| | |
|---|---|
| Propyl parahydroxybenzoate | 0.20 g |
| Water, permuted | 66.85 g |
| Mineral dyes | 5.00 g |
| | 105.00 g |

This example is repeated except that the polymer of Example 32 is replaced by the same amount of any one of the polymers of Examples 18–26 and 38–42.

EXAMPLE L

A hair rinse or conditioner composition in the form of a fluid emulsion is prepared by admixing the following components:

Petrolatum oil: 9.5 g
$C_{16}$–$C_{18}$ fatty alcohols polyglycerolated with 2–6 moles of glycerol: 6.5 g
Polymer of Example 18: 1.5 g
Water, q.s.p.: 100 g This product is applied to previously washed and dried hair by carefully distributing it on all of the hair and slightly massaging it therethrough. The composition is then permitted to remain in contact with the hair for about 2 minutes. Thereafter the hair is carefully rinsed and it exhibits a shiny luster and is easily untangled.

This example is repeated except that the polymer of Example 18 is replaced by the same quantity of any one of the polymers of Examples 28–35 and 38–43. Equally favorable results are achieved.

EXAMPLE M

A hair rinse composition in the form of a gel is prepared by admixing the following components:

Hydroxyethyl cellulose: 0.9 g
Polymer of Example 36: 0.8 g
Cetyl pyridinium chloride: 3 g
Dye, sufficient to color the gel: 0.1 g
Water, q.s.p.: 100 g This gel composition is applied to washed and dried hair by slightly massaging it therethrough. The composition is permitted to remain in contact with the hair for about 1–2 minutes. Thereafter the hair is carefully rinsed and the hair thus treated is shiny and is easily untangled.

This example is repeated except that the polymer of Example 36 is replaced by the same amount of any one of the polymers of Examples 45–52. Equally advantageous results are achieved.

EXAMPLE N

An anionic shampoo composition is prepared by admixing the following components:

Triethanolamine lauryl myristyl sulfate: 12 g
Copra diethanolamide: 2 g
Dimethylamine myristyl oxide: 1.5 g
Polymer of Example 20: 1.5 g
Lactic acid, q.s.p. pH = 6.5
Water, q.s.p.: 100 g This shampoo exhibits excellent cosmetic properties. After its application to the hair and removal by rinsing, the wet hair untangles very easily and the hair, after drying, it shiny, soft and flexible.

This example is repeated except that the polymer of Example 20 is replaced by the same amount of any one of the polymers of Examples 21, 22, 24, 30, 41, 43 and 44. Equally favorable results are achieved.

EXAMPLE O

A cationic shampoo composition is prepared by admixing the following components:

Cetyl trimethyl ammonium bromide: 2 g
Lauryl alcohol polyglycerolated with 4 moles of glycerol: 12 g
Polymer of Example 16: 1 g
Perfume: 0.2 g
Lactic acid, q.s.p. pH = 4.5
Water, q.s.p.: 100 ml This shampoo when applied to the hair provides a soft and aerated foam and provides very easy untangling of wet hair. After drying, the hair is soft, very bright and exhibits a light appearance.

This example is repeated except that the polymer of Example 16 is replaced by the same amount of any one of the polymers of Examples 21–25 and 32–36.

EXAMPLE P

A non-ionic shampoo composition is prepared by admixing the following components:

$C_{11}$–$C_{14}$ diol polyglycerolated with 3–4 moles of glycerol: 17 g
Polymer of Example 40: 2 g
Cetyl pyridinium chloride: 0.8 g
Lauryl diethanolamine: 2.5 g
Perfume: 0.2 g
Lactic acid, q.s.p. pH = 5.5
Water, q.s.p.: 100 ml This clear shampoo composition provides a sufficiently soft abundant foam and provides for easy untangling of wet hair, dyed or bleached. After drying the hair is soft, light and shiny.

This example is repeated except that the polymer of Example 40 is replaced by the same amount of any one of the polymers of Examples 41, 43 and 44.

EXAMPLE Q

A hair dye composition in the form of a gellable liquid is prepared as follows:

A hair dye base is prepared by admixing the following components:

Oleyl alcohol glycerolated with 2 moles of glycerol: 20 g
Oleyl alcohol glycerolated with 4 moles of glycerol: 20 g
Butyl glycol: 8 g
Propylene glycol: 12 g
Ammonia (22° Bé): 10 ml
Para-aminophenol base: 0.08 g
Meta-diaminoanisol sulfate: 0.025 g
Resorcin: 0.3 g
Meta-aminophenol base: 0.06 g
Nitro paraphenylene diamine: 0.003 g
Paratoluylene diamine: 1.05 g
Hydroquinone: 0.17 g
Ethylene diamine tetraacetic acid: 3 g
Sodium bisulfite (d = 1.32): 0.8 g
Water, q.s.p.: 100 g To 50 g of the above hair dye base there are mixed at the moment of use 5 g of a 35% solution of the polymer of Example 29 and 50 g of $H_2O_2$ (20 volumes).

The resulting composition is then applied to the hair with the aid of a brush and is permitted to remain in contact therewith for 30 minutes. Thereafter, the hair is thoroughly rinsed. The wet hair is easily untangled and when dried it has a soft feel or touch, is shiny and has body. On deep chestnut hair, a light chestnut coloration is achieved.

This example is repeated except that the polymer of Example 29 is replaced by an equivalent amount of any one of the polymers of Examples 16, 19-21, 23, 24, 26 and 35.

EXAMPLE R

An essentially colorless nail lacquer composition is prepared by admixing the following components:

| | |
|---|---|
| Nitrocellulose, RS ½ second viscosity | 16 g |
| Polymer of Example 50 | 6 g |
| Ethyl alcohol | 4 g |
| Butyl alcohol | 4 g |
| Camphor | 2 g |
| Butyl phthalate | 4 g |
| Toluene | 20 g |
| Ethyl acetate | 10 g |
| Butyl acetate | 34 g |
| | 100 g |

This nail lacquer or enamel when applied to the nails exhibits very good adhesion and excellent brightness for a prolonged period of time.

This example is repeated except that the polymer of Example 50 is replaced without inconvenience by any one of the polymers of Examples 40–44, 49 and 51.

EXAMPLE S

A colored nail lacquer or enamel is prepared by admixing the following components:

| | |
|---|---|
| The colorless nail lacquer of Example R | 96.88 g |
| Benzyl-dodecyl dimethyl-ammonium montmorillonite, Bentone 27 | 1 g |
| Phosphoric acid | 0.02 g |
| Titanium oxide | 1 g |
| D and C Red No. 7 | 0.4 g |
| D and C Red No. 11 | 0.2 g |
| D and C Red No. 5 | 0.3 g |
| Red iron oxide | 0.2 g |
| | 100 g |

This nail lacquer exhibits excellent brightness and very good adhesion.

What is claimed is:

1. A shampoo composition comprising an aqueous solution of a polymer produced by polymerizing an unsaturated monomer selected from the group consisting of
   (a) acrylic acid,
   (b) methacrylic acid
   (c) an ester of the formula

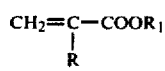

wherein R is hydrogen or methyl, and $R_1$ is linear or branched alkyl having 1-18 carbon atoms,
   (d) an ester of the formula

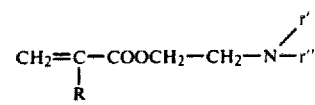

wherein R has the same meaning given above and r′ and r″ each independently represent alkyl having 1–5 carbon atoms and corresponding quaternary esters thereof,
   (e) an ester of the formula

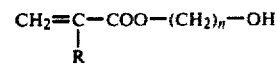

wherein R has the same meaning given above and n is 2 or 3,
   (f) acrylamide,
   (g) methacrylamide,
   (h) hydroxy alkylacrylamide of the formula

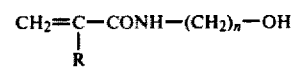

wherein R has the same meaning given above and n is 1–3,
   (i) a compound of the formula

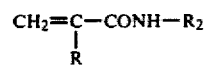

wherein R has the same meaning given above and $R_2$ represents linear or branched alkyl having 1–5 carbon atoms, and
   (j) a compound of the formula

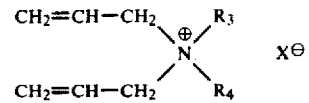

wherein $R_3$ and $R_4$ each independently represent linear or branched alkyl having 1–16 carbon atoms and X is Cl or Br,
with about 15 to 95 percent by weight of a compound based on the combined weight of said unsaturated monomer and said compound and selected from the group consisting of
   (1) a product selected from the group consisting of gelatin, cellulose, starch, collagen, chitosans, nitro-cellulose and cellulose ethers,
   (2) a polymer selected from the group consisting of polyvinyl alcohol, hydrolyzed polyvinyl acetate, hydrolyzed copolymer of N-vinylpyrrolidone and vinyl acetate, hydrolyzed copolymer of crotonic acid and vinyl acetate, polyvinylpyrrolidone having terminal OH groups, polyacrylamide having terminal OH groups, N,N-dimethyl-2-amino ethyl methacrylate having terminal OH groups and quaternized with ethyl bromide, polybutadiene having terminal OH groups, polyisobutylene having terminal OH groups, copolymer of N-vinylpyrrolidone and N-methacryloyl D-glucosamine and copolymer of N-vinylpyrrolidone and N-methacryloyl D-glucosamine having terminal OH groups, (3) a polymeric compound selected from the group consisting of polyethylene glycol and polypropylene glycol, and (4) pentaerythritol, said polymerization being carried out in an aqueous medium and in the presence of cerium ammonium nitrate at a temperature between ambient temperature and 80° C., and a cationic, nonionic or anionic detergent, said detergent being present in an amount between 5 and 50 weight percent of said composition and said polymer being present in an amount between 0.1 and 10 weight percent of said composition.

2. A method for shampooing the hair comprising applying to the hair an effective amount of the shampoo composition of claim 1 and then rinsing and drying the hair.

3. An aerosol hair lacquer composition packaged under pressure in an aerosol container comprising an alcoholic or hydroalcoholic solution of 0.1 to 3 weight percent of a polymer produced by polymerizing an unsaturated monomer selected from the group consisting of (a) acrylic acid, (b) methacrylic acid, (c) an ester of the formula

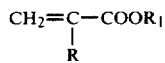

wherein R is hydrogen or methyl, and $R_1$ is linear or branched alkyl having 1-18 carbon atoms, (d) an ester of the formula

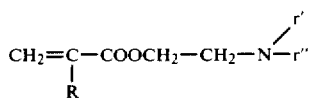

wherein R has the same meaning given above and r' and r" each independently represent alkyl having 1-5 carbon atoms and corresponding quaternary esters thereof, (e) an ester of the formula

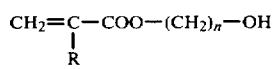

wherein R has the same meaning given above and n is 2 or 3, (f) acrylamide, (g) methacrylamide, (h) hydroxy alkylacrylamide of the formula

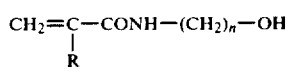

wherein R has the same meaning given above and n is 1-3, (i) a compound of the formula

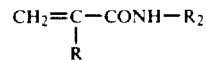

wherein R has the same meaning given above and $R_2$ represents linear or branched alkyl having 1-5 carbon atoms, and (j) a compound of the formula

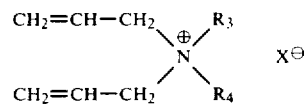

wherein $R_3$ and $R_4$ each independently represent linear or branched alkyl having 1-16 carbon atoms and X is Cl or Br, with about 15 to 95 percent by weight of a compound based on the combined weight of said unsaturated monomer and said compound and selected from the group consisting of (1) a product selected from the group consisting of gelatin, cellulose, starch, collagen, chitosans, nitro-cellulose and cellulose ethers, (2) a polymer selected from the group consisting of polyvinyl alcohol, hydrolyzed polyvinyl acetate, hydrolyzed copolymer of N-vinylpyrrolidone and vinyl acetate, hydrolyzed copolymer of crotonic acid and vinyl acetate, polyvinylpyrrolidone having terminal OH groups, polyacrylamide having terminal OH groups, N,N-dimethyl-2-amino ethyl methacrylate having terminal OH groups and quaternized with ethyl bromide, polybutadiene having terminal OH groups, polyisobutylene having terminal OH groups, copolymer of N-vinylpyrrolidone and N-methacryloyl D-glucosamine and copolymer of N-vinylpyrrolidone and N-methacryloyl D-glucosamine having terminal OH groups, (3) a polymeric compound selected from the group consisting of polyethylene glycol and polypropylene glycol, and (4) pentaerythritol, said polymerization being carried out in an aqueous medium and in the presence of cerium ammonium nitrate at a temperature between ambient temperature and 80° C., and an aerosol propellant.

4. A method for treating the hair comprising spraying the hair with an effective amount of the aerosol hair lacquer composition of claim 3.

5. A cream for application to the skin to improve the appearance thereof comprising an oily phase emulsified with an aqueous phase containing in solution 0.1 to 10 weight percent of a polymer produced by polymerizing an unsaturated monomer selected from the group consisting of (a) acrylic acid, (b) methacrylic acid, (c) an ester of the formula

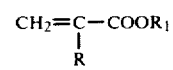

wherein R is hydrogen or methyl, and $R_1$ is linear or branched alkyl having 1-18 carbon atoms, (d) an ester of the formula

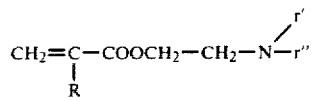

wherein R has the same meaning given above and r' and r" each independently represent alkyl having 1–5 carbon atoms and corresponding quaternary esters thereof, (e) an ester of the formula

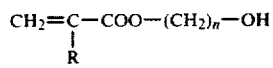

wherein R has the same meaning given above and n is 2 or 3, (f) acrylamide,
(g) methacrylamide,
(h) hydroxy alkylacrylamide of the formula

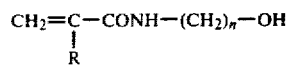

wherein R has the same meaning given above and n is 1–3, (i) a compound of the formula

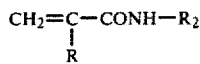

wherein R has the same meaning given above and $R_2$ represents linear or branched alkyl having 1–5 carbon atoms, and (j) a compound of the formula

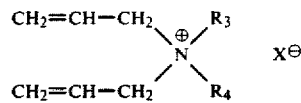

wherein $R_3$ and $R_4$ each independently represent linear or branched alkyl having 1–16 carbon atoms and X is Cl or Br, with about 15 to 95 percent by weight of a compound based on the combined weight of said unsaturated monomer and said compound and selected from the group consisting of (1) a product selected from the group consisting of gelatin, cellulose, starch, collagen, chitosans, nitro-cellulose and cellulose ethers, (2) a polymer selected from the group consisting of polyvinyl alcohol, hydrolyzed polyvinyl acetate, hydrolyzed copolymer of N-vinylpyrrolidone and vinyl acetate, hydrolyzed copolymer of crotonic acid and vinyl acetate, polyvinylpyrrolidone having terminal OH groups, polyacrylamide having terminal OH groups, N,N-dimethyl-2-amino ethyl methacrylate having terminal OH groups and quaternized with ethyl bromide, polybutadiene having terminal OH groups, polyisobutylene having terminal OH groups, copolymer of N-vinylpyrrolidone and N-methacryloyl D-glucosamine and copolymer of N-vinylpyrrolidone and N-methacryloyl D-glucosamine having terminal OH groups, (3) a polymeric compound selected from the group consisting of polyethylene glycol and polypropylene glycol, and (4) pentaerythritol, said polymerization being carried out in an aqueous medium and in the presence of cerium ammonium nitrate at a temperature between ambient temperature and 80° C.

6. The composition of claim 5 wherein said oily phase is selected from the group consisting of paraffin oil, petrolatum oil, sweet almond oil, avocado oil, olive oil, glyceryl monostearate, ethyl palmitate isopropyl palmitate, propyl myristate, butyl myristate and cetyl myristate.

7. A method for treating the skin comprising applying thereto an effective amount of the skin cream composition of claim 5.

8. A method for treating the hair or skin to improve the appearance thereof comprising applying to the hair or skin an effective amount of a cosmetic composition for said hair or skin which contains in an appropriate cosmetic vehicle selected from water, alcohol or a hydroalcoholic solution 0.1 to 15 weight percent of a polymer produced by polymerizing from 5% to about 85% by weight of an unsaturated monomer selected from the group consisting of (a) acrylic acid,
(b) methacrylic acid,
(c) an ester of the formula

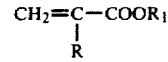

wherein R is hydrogen or methyl, and $R_1$ is linear or branched alkyl having 1–18 carbon atoms, (d) an ester of the formula

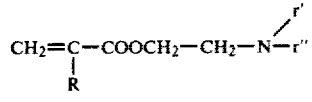

wherein R has the same meaning given above and r' and r" each independently represent alkyl having 1–5 carbon atoms and corresponding quaternary esters thereof, (e) an ester of the formula

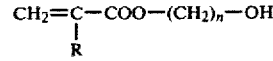

wherein R has the same meaning given above and n is 2 or 3, (f) acrylamide,
(g) methacrylamide,
(h) hydroxy alkylacrylamide of the formula

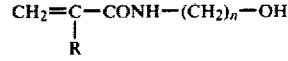

wherein R has the same meaning given above and n is 1–3, (i) a compound of the formula

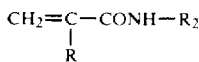

wherein R has the same meaning given above and R$_2$ represents linear or branched alkyl having 1-5 carbon atoms, and (j) a compound of the formula

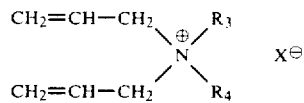

wherein R$_3$ and R$_4$ each independently represent linear or branched alkyl having 1-16 carbon atoms and X is Cl or Br, with about 15 to 95 percent by weight of a compound based on the combined weight of said monomer and said compound and selected from the group consisting of (1) a product selected from the group consisting of gelatin, cellulose, starch, collagen, chitosans, nitro-cellulose and cellulose ethers, (2) a polymer selected from the group consisting of polyvinyl alcohol, hydrolyzed polyvinyl acetate, hydrolyzed copolymer of N-vinylpyrrolidone and vinyl acetate, hydrolyzed copolymer of crotonic acid and vinyl acetate, polyvinylpyrrolidone having terminal OH groups, polyacrylamide having terminal OH groups, N,N-dimethyl-2-amino ethyl methacrylate having terminal OH groups and quaternized with ethyl bromide, polybutadiene having terminal OH groups, polyisobutylene having terminal OH groups, copolymer of N-vinylpyrrolidone and N-methacryloyl D-glucosamine and copolymer of N-vinylpyrrolidone and N-methacryloyl D-glucosamine having terminal OH groups, (3) a polymeric compound selected from the group consisting of polyethylene glycol and polypropylene glycol, and (4) pentaerythritol, wherein said polymerization is carried out in an aqueous medium and in the presence of cerium ammonium nitrate at a temperature between ambient temperature and 80° C.

9. A method for treating the hair to improve the appearance thereof comprising applying to damp hair an effective amount of an cosmetic composition for said hair which is a solution in water or in a hydroalcoholic solution of 0.1 to 10 weight percent of a polymer produced by polymerizing from 5% to about 85% by weight of an unsaturated monomer selected from the group consisting of (a) acrylic acid, (b) methacrylic acid, ·

(c) an ester of the formula

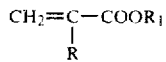

wherein R is hydrogen or methyl, and R$_1$ is linear or branched alkyl having 1-18 carbon atoms, (d) an ester of the formula

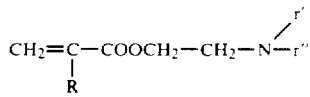

wherein R has the same meaning given above and r' and r" each independently represent alkyl having 1-5 carbon atoms and corresponding quaternary esters thereof, (e) an ester of the formula

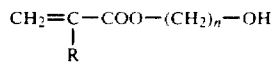

wherein R has the same meaning given above and n is 2 or 3, (f) acrylamide, (g) methacrylamide, (h) hydroxy alkylacrylamide of the formula

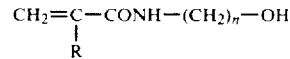

wherein R has the same meaning given above and n is 1-3, (i) a compound of the formula

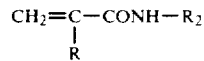

wherein R has the same meaning given above and R$_2$ represents linear or branched alkyl having 1-5 carbon atoms, and (j) a compound of the formula

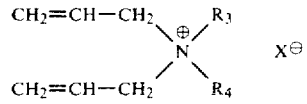

wherein R$_3$ and R$_4$ each independently represent linear or branched alkyl having 1-16 carbon atoms and X is Cl or Br, with about 15 to 95 percent by weight of a compound based on the combined weight of said monomer and said compound and selected from the group consisting of (1) a product selected from the group consisting of gelatin, cellulose, starch, collagen, chitosans, nitro-cellulose and cellulose ethers, (2) a polymer selected from the group consisting of polyvinyl alcohol, hydrolyzed polyvinyl acetate, hydrolyzed copolymer of N-vinylpyrrolidone and vinyl acetate, hydrolyzed copolymer of crotonic acid and vinyl acetate, polyvinylpyrrolidone having terminal OH groups, polyacrylamide having terminal OH groups, N,N-dimethyl-2-amino ethyl methacrylate having terminal OH groups and quaternized with ethyl bromide, polybutadiene having terminal OH groups, polyisobutylene having terminal OH groups, copolymer of N-vinylpyrrolidone and N-methacryloyl D-glucosamine and copolymer of N-vinylpyrrolidone and N-methacryloyl D-glucosamine having terminal OH groups,
(3) a polymeric compound selected from the group consisting of polyethylene glycol and polypropylene glycol, and
(4) pentaerythritol, wherein said polymerization is carried out in an aqueous medium and in the presence of cerium ammonium nitrate at a temperature between ambient temperature and 80° C.

said composition having a pH from 6 to 8, permitting said composition to remain in contact with said hair for 3 to 15 minutes and thoroughly rinsing said hair.

10. A method for treating the hair or skin to improve the appearance thereof comprising applying to the hair or skin an effective amount of a cosmetic composition for the hair or skin comprising a cosmetic vehicle selected from the group consisting of water, alcohol and a hydroalcoholic solution and 0.1 to 15 weight percent of a polymer produced by polymerizing from 5 to about 85 percent by weight of an unsaturated monomer selected from the group consisting of methyl methacrylate, lauryl methacrylate, hexyl methacrylate, N,N-dimethyl-2-aminoethyl polymethacrylate quaternized with dimethyl sulfate, N,N-dimethyl-2-aminoethyl methacrylate quaternized with ethyl bromide, acrylic acid, acrylamide and N-terti. butyl acrylamide, with about 15 to 95 percent by weight of a compound based on the combined weight of said unsaturated monomer and said compound, said compound being selected from the group consisting of gelatin, methyl cellulose, methyl hydroxy propyl cellulose, hydroxyethyl cellulose, methyl hydroxy butyl cellulose, carboxy methyl cellulose, collagen, polyvinylpyrrolidone having terminal OH groups, copolymer of N-vinylpyrrolidone and N-methacryloyl D-glucosamine having terminal OH groups, copolymer of N-vinylpyrrolidone and N-methacryloyl D-glucosamine, hydrolyzed copolymer of N-vinylpyrrolidone and vinyl acetate, hydrolyzed copolymer of crotonic acid and vinyl acetate, N,N-dimethylamino-2-ethyl methacrylate having terminal OH groups and quaternized with ethyl bromide, polyvinyl alcohol, polyethylene glycol and pentaerythritol, said polymerization being carried out in an aqueous medium and in the presence of cerium ammonium nitrate at a temperature between ambient temperature and 80° C.

* * * * *